United States Patent [19]

Kokal, Jr.

[11] 4,026,027

[45] May 31, 1977

[54] DENTAL HAND DRILL EMPLOYING PRESSURE-SENSITIVE GRIP

[76] Inventor: August Kokal, Jr., 8710 Lone Star Road, Jacksonville, Fla. 32211

[22] Filed: Mar. 7, 1975

[21] Appl. No.: 556,460

[52] U.S. Cl. .................................................. 32/26
[51] Int. Cl.² ........................................... A61C 1/08
[58] Field of Search ............ 32/26, 27, DIG. 3, 28, 32/DIG. 1; 310/50, 68 A

[56] References Cited

UNITED STATES PATENTS

| | | | |
|---|---|---|---|
| 2,924,114 | 2/1960 | Hitt et al. | 415/503 |
| 3,346,958 | 10/1967 | Sinatra et al. | 32/28 |
| 3,423,068 | 1/1969 | Hall | 32/27 |
| 3,842,504 | 10/1974 | Ricks | 32/27 |
| 3,955,283 | 5/1976 | Mehallick | 32/26 |

Primary Examiner—Hugh R. Chamblee
Assistant Examiner—Peter K. Skiff
Attorney, Agent, or Firm—Berman, Aisenberg & Platt

[57] ABSTRACT

A pressure-sensitive grip for a dental hand drill for providing continuous control of the speed thereof. The pressure-sensitive material preferably comprises a strain gage sensing element positioned along the body portion of the dental tool which is normally hand held by the operator. In a fluid-driven dental tool, the strain gage is coupled through a control network which provides an electrical signal to control a proportional valve in the fluid supply line to the drill.

13 Claims, 4 Drawing Figures

DENTAL HAND DRILL EMPLOYING PRESSURE-SENSITIVE GRIP

BACKGROUND OF THE INVENTION

1. Field of the Invention

This invention is directed toward improvements in fluid-driven rotary dental tools and, more particularly, is related to a pressure-sensitive grip for a dental hand drill which allows the operator to easily, accurately and continuously control the speed of the drill.

2. Description of the Prior Art

There exists many different control mechanisms and techniques for controlling the pressure fluid to pneumatic motors of power operated tools such as those utilized to control the air in a compressed air turbine driven dental drilling machine. Some of such control mechanisms incorporate foot actuated switches or valves which control the supply of electricity or air via a control valve. Such foot pedal mechanisms have long been recognized as being less than desirable owing to various annoyances and inconveniences as pointed out in the U.S. patent to Kopp (No. 3,244,846).

As a result of the recognized deficiencies of foot switches, pedals, and the like, subsequent artisans have proposed the fitting of electric switches and control mechanisms on the hand or angle piece of the drill, as exemplified by the Kopp patent. Unfortunately, such prior art attempts have been less than entirely successful in providing an inexpensive, convenient, easily operable precision device for controlling the speed of the drill. One of the main difficulties of prior art control mechanisms as exemplified by said Kopp patent, the White patent (No. 3,256,603), and the Coss patent (No. 3,430,710) is the apparent failure to provide a means for minutely and continuously regulating the supply of air pressure, and hence the speed of the pneumatic motor or turbine of the drill, over a wide range of desired limits which is both inexpensive and noncomplex. Other prior U.S. Patents in this area of which I am aware include the Prufer Pat. No. 3,210,847, and the Martin Pat. No. 3,568,318. However, neither of the foregoing provide the concommitant requirements of reliability in operation and ease of use so necessary in tools of this nature.

OBJECTS AND SUMMARY OF THE INVENTION

It is therefore a primary object of the present invention to provide a novel and unique means for controlling the speed of a fluid-driven rotary dental tool which overcomes all of the above-cited and other disadvantages of prior art mechanisms of this nature. Another object of the present invention is to provide an improvement for standard fluid-driven rotary dental tools, which improvement comprises means for continuously and directly controlling the speed of the dental tool which features ease of operation and reliability in use.

An additional object of the present invention is to provide a means for controlling the speed of compressed air turbine driven dental drilling machines by means of a well known electromechanical component incorporated into the hand held portion of the dental drill.

A still further object of the present invention is to provide in a pneumatically driven hand tool such as a dental drill a simple, convenient, and reliable technique for controlling the speed of the drill in a manner more natural to the operator and therefore less distractive than those of the prior art.

The foregoing and other objects are achieved in accordance with one aspect of the present invention through the provision of a pressure-sensitive means, such as a strain gage element, integrally formed in the elongated body of the dental tool. The pressure-sensitive strain gage element is positioned so as to be gripped by the hand of the operator during normal drilling operations. The electrical resistance of the element changes as a function of the manual pressure imparted thereagainst by the operator. The resistance change may be utilized in a control circuit so as to deliver an electrical output signal for controlling the position of a proportional valve disposed in the pressurized supply line to the drill. Several preferred embodiment mounting arrangements for the strain gate element along the elongated body of the dental tool are disclosed.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF THE PREFERRED EMBODIMENT

Figure 1:
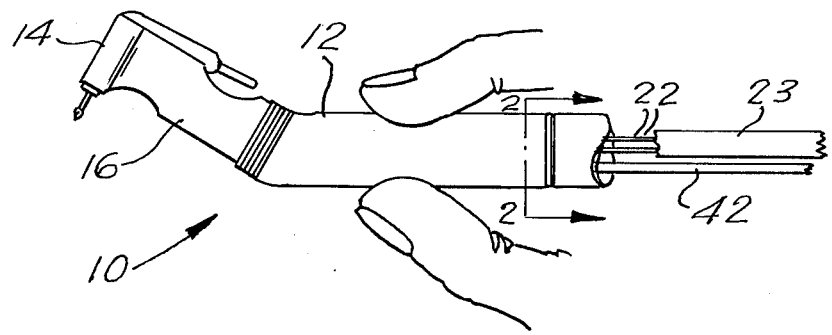
FIG. 1 is a diagrammatic side view of a rotary dental tool and its associated pressure-sensitive hand grip according to a preferred embodiment of the present invention.

Referring now to the drawings, wherein like reference numerals represent identical or corresponding parts throughout the several views, and more particularly to FIG. 1 thereof, there is indicated generally at 10 the pressure-sensitive hand grip incorporated into a conventional fluid-driven rotary dental tool in accordance with one preferred embodiment of the present invention.

Hand grip 10 is seen to comprise an elongated pressure-sensitive body 12 which is adapted to be manually held by the user/operator thereof. Extending from the hand held body 12 is an angular housing 16, the other end of which supports the head 14 of the drill which houses the air turbines, in the conventional manner. The speed of the air turbine within head 14 of the dental drill is directly proportional to the amount of compressed air delivered thereto via inlet conduit 42 which is generally disposed within the tool housing.

The pressure-sensitive means 12 preferably comprises an integrally formed strain gage sensing element. Such strain gage elements have the well-known property of changing their electrical resistance in direct proportion to a change in length, within limits prescribed by the individual strain gage material and geometry. As is well known, the sensitivity of a strain gage is measured in terms of the ratio of the change in resistance for each unit of resistance in the sensing element to the strain imposed on the sensing element. Such a ratio, commonly known as the "gage factor", represents an intrinsic quality of the sensing element which varies from one material to another even though the shape and dimensions of each material are the same. Of the two types of strain gage elements presently available, I have found that within the context of the present invention a semiconductor strain gage would be preferable over a metallic type strain gage, although the latter type may prove advantageous in certain situations. Since a semiconductor strain gage exhibits a much larger change in resistance for a given level of strain, i.e., semiconductor strain gages are much more sensitive than metallic strain gages, the former are frequently better adapted to provide the kind of continuous and precision control necessary for the operation of the pneumatic hand tools of the present invention. However, for the sake of simplicity, hereinafter the present invention will be described in connection with a general strain gage of either the semiconductor or metallic variety, it being understood that the principles of the present invention are not limited to either type but rather comprehend any of the well-known strain gage materials which will suggest themselves to a person of ordinary skill in the art.

Thus, in accordance with the present invention, a strain gage in employed as the pressure-sensitive means 12. The strain gage may be mounted in any of several alternative embodiments. For example, with reference to FIG. 2, the strain gage 24 is shown attached, by means of a well known suitable adhesive, to an inner sleeve 20 of a floating grip embodiment. Relatively rigid inner sleeve 20 is positioned coaxially with a relatively flexible outer sleeve 25. Disposed between inner sleeve 20 and outer sleeve 25 is a fluid medium 18. Extending from strain gage 24 are a pair of electrical lead wires 22 which extend through an aperture 28 formed in a support disc or cylinder 26. The strain gage of FIG. 2 preferably takes the form of a wire or foil strain gage capable of sensing the compressive radial strain on the periphery of handle 10. In operation of this embodiment, any change in pressure on the external periphery of flexible outer sleeve 25 is transmitted via the fluid medium 18 and the inner sleeve 20 to the strain gage 24. This causes a change in the electrical resistance thereof which accordingly modifies the current through leads 22, such current modification to be utilized in a manner to be described in more detail hereinafter.

Figure 2:
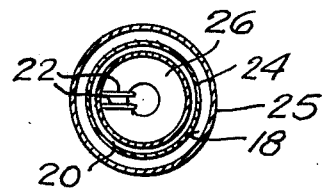
FIG. 2 is a cross-sectional view of the apparatus depicted in FIG. 1 taken along lines 2—2 thereof.
Figure 3:
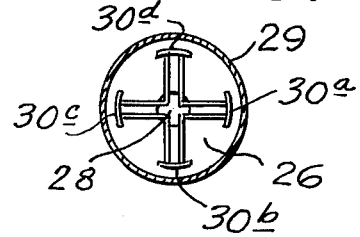
FIG. 3 is a cross-sectional view similar to that shown in FIG. 2 but of an alternative preferred embodiment of the present invention.

Referring now to FIG. 3, a cross-sectional view of an alternative embodiment to that shown in FIG. 2 is illustrated. In this embodiment, the strain gage is illustrated as of the semiconductor variety and includes several elements 30a, 30b, 30c and 30d mounted to the inside wall of a metal sleeve 29 which forms the outer surface of the elongated body 12. As previously, lead wires 22 extend from strain gages 30a–30d through an aperture 28 formed in a support disc or cylinder 26. Semiconductor crystals suitable for use as the strain gage elements in accordance with the present invention include those conventional strain gages available from, for example, BLH Electronics, Inc., of Waltham, Mass. General examples of such semiconductor strain gages may be found in their Bulletin No. 102-2"SR-4Semiconductor Strain Gages", and a particularly comprehensive theoretical and practical treatment of same may be found in their "Semiconductor Strain Gage Handbook".

A third alternative to the embodiments depicted in FIGS. 2 and 3 is to have the strain gage element mounted and exposed directly on the surface of the elongated body member 12. Many other configurations will suggest themselves to a person of ordinary skill in the art, and it is to be understood that those described in conjunction with FIGS. 1 through 3 are intended to be only exemplary of such configurations.

Figure 4:
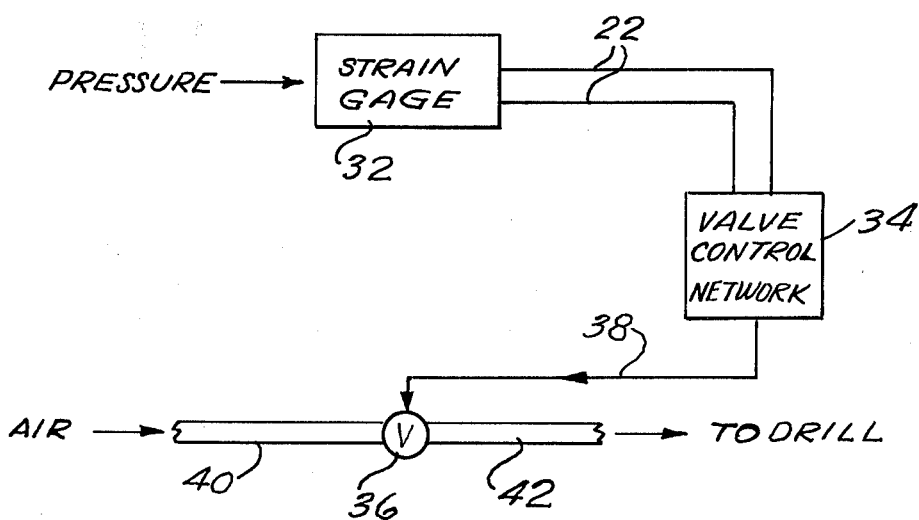
FIG. 4 is a partial schematic, partial block diagram of the basic components of the system in accordance with the present invention.

Referring now to FIG. 4, the operation of the dental drilling machine in accordance with the strain gage pressure-sensitive grip will now be explained. As explained above, strain gage 32 responds to changes in input pressure by changing its electrical resistance. This change in electrical resistance may be detected along output leads 22. A valve control network 34 may be provided to convert the change in resistance to a current or voltage control signal which is delivered along output line 38. A proportional valve 36 is responsive to the current or voltage control signal along line 38 by varying its aperture to thereby vary the amount of fluid, in this instance air, delivered from input conduit 40 to output conduit 42. In this manner, the speed of the drill, directly proportional to the volume of compressed air delivered to the turbine 14, may be simply and reliably controlled by virtue of the manual pressure exerted on handle 12 of the pneumatic dental drill.

Valve control network 34 comprehends any of a number of well-known electrical and/or electronic circuits which are current responsive to deliver output signals indicative thereof. Many configurations will suggest themselves to a person of ordinary skill in the art. For example, strain gage 32 may be connected as the unknown resistance element in one arm of a Wheatstone bridge circuit, the output of which may be connected to, for example, an operational amplifier having a feedback path which includes the electrically responsive air control valve 36.

Air control valve 36 may be comprised of any of a number of well-known modulating valves, also known as proportional valves, which respond continuously to a change in electrical input voltage or current by either increasing or decreasing its valve opening. Exemplary valves suitable for use as air control valve 36 are the series 1400 single-seated valves manufactured by Honeywell International of Fort Washington, Pa. Thus, the system of the present invention may be thought of as a double-transducer system wherein the manual pressure exerted by the operator is first transduced into an electrical quantity which is subsequently transduced into a fluid quantity.

It is therefore seen that I have provided a novel and unique control means for a pneumatically operated compressed air dental tool which requires few moving parts, is economical to construct and operate, is straightforward and reliable in its operation, and which may be adapted to great advantage by using existing technology. The only part that need be mounted in the hand tool itself is the strain gage element. The leads 22 may extend therefrom, enclosed by a flexible sleeve 23 as seen in FIG. 1, to an appropriate external control unit which may house the valve control network 34 and the air control valve 36. Such a construction eliminates the weighty bulkiness associated with prior art devices which require the valve to be mounted in the handle of the tool itself.

Modifications of the present invention include the provision of a second transducer rearwardly of the handle-grip region 10 which may be utilized to actuate an ON-OFF switch to control a coolant spray, such as water, which is necessary during dental drilling. Further, a water control valve could be separately provided to control the flow rate of the water which, once adjusted to each operator's personal liking, should require no further adjustment. The usual variety of secondary controls, such as emergency shut-off switches, dental chair and operator's stool control, and assistance call button may also be included in a system embodying the present invention. It should be understood that any or all of such further controls may be embodied in a like or similar manner to that just described in connection with the pressure-sensitive speed control.

Since it is apparent that numerous modifications and variations of the present invention are possible in light of the above teachings, I wish it to be understood that I do not desire to be limited to the exact details shown and described, for within the scope of the appended claims the invention may be practiced otherwise than as specifically described herein.

I claim:

1. In a fluid-driven rotary dental tool which includes an elongated body manipulatable by one hand of the operator, the improvement which comprises pressure-sensitive means integrally formed in said body for continuously controlling the speed of said rotary dental tool in proportion to the manual pressure exerted thereon by said operator, said pressure-sensitive means comprising a material whose electrical resistance changes in proportion to its change in length.

2. The dental tool as set forth in claim 1 wherein said material comprises a strain gage sensing element.

3. The dental tool as set forth in claim 2 wherein said strain gage sensing element comprises a semiconductor.

4. The dental tool as set forth in claim 3 further comprising means responsive to said change in electrical resistance for varying the speed of said tool.

5. The dental tool as set forth in claim 4 wherein said speed varying means includes an electrical control means operatively connected to the output leads of said semiconductor strain gage for producing an electrical control signal in response thereto.

6. The dental tool as set forth in claim 5 wherein said speed varying means further includes valve means responsive to said control signal for varying the amount of fluid delivered from a fluid source of supply to said rotary dental tool whereby the speed of the latter may be controlled.

7. The dental tool as set forth in claim 3, wherein said semiconductor strain gage is positioned on the outer periphery of a manipulatable portion of said elongated body.

8. The dental tool as set forth in claim 3, wherein said semiconductor strain gage is cylindrically shaped and is positioned inwardly adjacent a metallic sleeve which extends along a manipulatable portion of said elongated body.

9. The dental tool as set forth in claim 3, wherein said semiconductor strain gage is substantially cylindrical and is positioned adjacent the inner surface of a fluid actuation cylinder means for transmitting manually provided pressure to said strain gage.

10. The dental tool as set forth in claim 9, wherein said fluid actuation cylinder means comprises an inner relatively rigid cylindrical member, an outer relatively flexible cylindrical member adapted to be manually held by said operator, and a fluid medium interposed between said inner and outer cylindrical members.

11. The dental tool as set forth in claim 6 further comprising an ON-OFF switch means for controlling the flow of fluid through said body of said tool.

12. The dental tool as set forth in claim 11 wherein said ON-OFF switch means comprises a second pressure-sensitive transducer positioned remote from said body.

13. A fluid-driven rotary dental tool which comprises an elongated body manipulatable by one hand of the operator, and strain-gage means integrally formed in said body for continuously controlling the speed of said rotary dental tool in proportion to the manual pressure exerted thereon by said operator.

* * * * *